United States Patent [19]
Friedman et al.

[11] Patent Number: 5,607,967
[45] Date of Patent: Mar. 4, 1997

[54] TREATMENT OF ALZHEIMER'S DISEASE WITH 5-(TETRADECYLOXY)-2-FURAN CARBOXYLIC ACID

[75] Inventors: Eitan Friedman, Wynnewood; M. Katharine Holloway, Lansdale; Gideon A. Rodan; Azriel Schmidt, both of Bryn Mawr; Robert L. Vogel, Richboro, all of Pa.

[73] Assignee: Merck & Co., Inc., Rahway, N.J.

[21] Appl. No.: 330,518

[22] Filed: Oct. 27, 1994

[51] Int. Cl.$^6$ ............................................. A61K 31/34
[52] U.S. Cl. .................................... 514/461; 514/473
[58] Field of Search ............................ 514/461, 212, 514/473

[56] References Cited

U.S. PATENT DOCUMENTS 4,981,784  1/1991  Evans et al. .................................. 435/6

OTHER PUBLICATIONS

Arbeeny, "Inhibition of fatty acid synthesis decreases renal low density lipoprotein secretion in the hamster", J. Lipid Res. 33: 843–851 (1992).

Ribeneau–Gyon and Gilles, FEBS Lett. 62: 309–312 (1976).

Halvorson and McCune, "Inhibition of fatty acid synthesis in isolated adipocytes by 5–(tetradecyloxy)–2–furoric acid", Lipids 19(11): 851–856 (1984).

Otto et al., "Reciprocal effects of 5–(tetradecyloxy)–2–fuoric acid on fatty acid oxidation", Arch. Biochem. Biophys. 242(1): 23–31, (1985).

Parker et al., "5–(tetradecyloxy)–2–furancarboxylic acid and related hypolipidemic fatty acid–like alkyloxyarylcarboxylic acids", J. Med. Chem. 20: 781–791 (1977).

Davis et al., "Transcriptional activation by Nur77, a growth factor inducible member of the steroid hormone receptor superfamily" Mol. Endocriniol. 5(6): 854–859, 1991.

Olson, "Reparative strategies in brain–treatment strategies based on trophic factors and cell transfer techniques", Acta Neurochirurgica 58: 3–7, 1993.

Seiger et al., "Intercranial infusion of purified nerve growth factor to an alzheimer patient" Behaviorial Brain Research 57:255–261, 1993.

Power, et al., "Dopamine activation of an orphan of the steroid receptor superfamily", Science 254, pp. 1546–1548, 1991.

Power et al., "New Insights into activation of the steroid hormone receptor superfamily", Trends Pharmacol. Sci. 13(8): 318–323, 1992.

Power et al., "Dopaminergic and igand–independent activation of steroid hormone receptors", Science 254; 1636–1639, 1991.

Lomax and Daniel, "Cocaine and body temperature in the rat: effect of dopamine D1 antagonists", Proc. west Pharmacol. Soc. 34:5–9, 1991.

Witkin et al. "Interaction of haloperidol and SCH23390 with cocaine and dopamine receptor subtype–selective agonists on schedule–controlled behavior of squirrel monkeys", Psychopharmacology Berl. 104(4):452–431, 1991.

Virno et al., "Dopamine, dopaminergic drugs and ocular hypertension", Int. Ophthalmol 16(4–5) 349–353, 1992.

Boyson and Alexander, "Net Production of cerebrospinal fluid is decreased by SCH22390", Ann. Neurol. 27(6): 631–635, 1990.

Lee and Kerlavage, "Molecular biology of G–protein–coupled receptors", Drug News Perspec. 6(7): 488–497, 1993.

Stryer and Bourne, "G proteins, a family of signal transducers", Ann. Rev. Cell. Biol. 2: 391–419, 1986.

Chao et al., "Gene Transfer and Molecular Cloning of the Human NGF Receptor" Science 232: 518–521, 1986.

Levi–Montalcini and Calissano, "The Nerve–Growth Factor" Sci. Amer. 240(6): 68–77. 1979.

Gilman, "G Proteins: Transducers of Receptor–Generated Signals" Ann. Rev. Bichem. 56: 615–49, 1987.

McGurk et al. "Dopaminergic Drugs Reverse the Impairment of Radiol–Arm Maze Performance Caused by Lesions Involving the Cholinergic Medial Pathway", Neuroscience vol. 50, No. 1 pp. 129–135 (1992).

*Primary Examiner*—Theodore J. Criares
*Attorney, Agent, or Firm*—Carol S. Quagliato; Catherine D. Fitch; Melvin Winokur

[57] ABSTRACT

Use of the novel receptor NER TOFA (5-(tetradecyloxy)-2-furan-carboxylic acid) to treat Alzheimer's disease.

5 Claims, No Drawings

TREATMENT OF ALZHEIMER'S DISEASE WITH 5-(TETRADECYLOXY)-2-FURAN CARBOXYLIC ACID

SUMMARY OF THE INVENTION

The present invention relates generally to a method of finding potentiators of receptors employing a screening procedure using the novel recombinant human steroid hormone receptor hereinafter called NER. The compound TOFA (5-(tetradecyloxy)-2-furan carboxylic acid) has been found through the above screening procedure employing NER to be a potentiator of ligands for other receptors, particularly G-protein coupled receptors, without having any independent effect on the receptors.

Compounds which activate the NER receptor, such as TOFA, potentiate the effects of nerve growth factor (NGF) and may be useful in the treatment of Alzheimer's disease. These compounds may also be useful in potentiating the effects of muscarinic agonists in the treatment of ocular hypertension. Further, compounds which activate the NER receptor are also useful in potentiating the effects of dopamine D1 antagonists in the treatment of psychoses, particularly schizophrenia, and in the treatment of movement disorders such as distonia, tardive dyskinesia and Gilles de la Tourette syndrome. Further NER activators may potentiate the prevention of the development of intraocular pressure induced by dopamine agonists in hydrodynamic disorders of the eye and in patients with increased intracranial pressure.

The novel recombinant steroid hormone receptor NER has been prepared by polymerase chain reaction techniques. Also disclosed are the complete sequence of human NER complementary DNA; expression systems, including a COS-stable expression system; and an assay using the COS expression system. In addition, the invention relates to a method for identifying functional ligands of the NER receptor.

BACKGROUND OF THE INVENTION

Retinoids, steroid and thyroid hormones and possibly other molecules produce their biological effects by binding to proteins of the steroid receptor superfamily. These receptors interact with specific DNA sequences and modulate gene expression (for reviews see J. M. Berg, Cell 57:1065–1068 (1989); R. M. Evans, Science 240:899–895 (1988); M. Beato, Cell 56:335–344 (1989)). Sequence analysis and functional studies of these receptors revealed two important regions which exhibit a high degree of amino acid residue conservation. The highest level of similarity among the receptors is found in a region which contains nine cysteine residues that bind zinc atoms to form two "zinc fingers," which interact with the cognate steroid response elements of DNA (J. Miller, et al., EMBO J 4:1609–1614 (1985); R. M. Evans, Cell 52:1–3 (1988)). The second region, which is less conserved, is the ligand-binding domain, responsible for the interaction with the hormone (J. Carlstedt-Duke, et al., Proc Natl Acad Sci USA 79:4260–4264 (1982). J. Carlstedt-Duke, et al., Proc Natl Acad Sci USA 84:4437–4440 (1987)). Recent studies have attributed additional functions to other domains of these receptors, such as protein-protein interaction that participates in transcriptional regulation (R. Scule, et al., Cell 62:1217–1226 (1990); H. F. Yang, Cell 62:1205–1215 (1990); J. M. Holloway et al., Proc Natl Acad Sci USA 87:8160–8164 (1990)). The amino acid conservation in the DNA binding domain has led to the identification of new members of the steroid receptor superfamily.

For example, hER1 and hER2 have been cloned by low stringency hybridization of cDNA libraries with a DNA probe coding for the DNA binding domain of the estrogen receptor (Giguere, et al., Nature 331:91–94 (1988)). Similar approaches have led to the discovery of the retinoic acid receptors and the peroxisome proliferator activator receptor (PPAR) (I. Issemann, et al., Nature 347:645–650 (1990); D. J. Mangelsdorf, et al., Nature 345:224–229 (1990)). Recently, three novel members of the Xenopus nuclear hormone receptor superfamily have been disclosed (C. Dreyer, Cell 68:879–887 (1992)). In addition, U.S. Pat. No. 4,981,784 to Evans, et al. discloses the identification of a retinoic acid receptor and the use of chimeric constructs to produce hybrid receptors for the identification of novel ligands. The above references, however, neither disclose nor suggest the instant invention.

TOFA (5-(tetradecyloxy)-2-furan-carboxylic acid) has been reported to inhibit fatty acid synthesis by inhibiting acetyl-CoA carboxylase, the rate limiting step in de novo fatty acid synthesis, in vivo

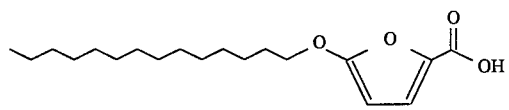

TOFA (5-(tetradecyloxy)-2-furancarboxylic acid)

at high doses, i.e. 0.15% of diet. (See, e.g. Arbeeny, "Inhibition of fatty acid synthesis decreases renal low density lipoprotein secretion in the hamster," J. Lipid Res. 33: 843–851, (1992); Ribeneau-Gyon and Gilles, FEBS Lett. 62: 309–312, (1976); Halvorson and McCune, "Inhibition of fatty acid synthesis in isolated adipocytes by 5-(tetradecyloxy)-2-furoic acid," Lipids 19(11): 851–856, (1984); Otto et al., "Reciprocal effects of 5-(tetradecyloxy)-2-fuoric acid on fatty acid oxidation," Arch. Biochem. Biophys. 242(1):23–31, (1985); Parker et al., "5-(tetradecyloxy)-2-furancarboxylic acid and related hypolipidemic fatty acid-like alkyloxyarylcarboxylic acids," J. Med. Chem. 20:781–791, 1977). The present invention comprises in one embodiment the use of low-dose TOFA to potentiate the activity of ligands of G-coupled receptors and to potentiate the activity of endogenously produced hormones or neurotransmitters.

Powell et al., ("Dopamine activation of an orphan of the steroid receptor family" Science 252: 1546–48, (1991), and "Dopaminergic and ligand independent activation of steroid hormone receptors" Science 254: 1636–39, (1991) have reported that dopamine activates transcription, mediated by steroid hormone receptors, by a ligand-independent mechanism. However, unlike dopamine, TOFA and activators of NER do not themselves have dopaminergic activity at the dosage level used.

Dopamine receptors are membrane proteins that have seven transmembrane domains and mediate transmembrane signaling via the heterotrimeric G proteins. The receptors are predominantly localized in the central nervous system, but peripheral organs such as the kidney, lower esophagus and cardiac and mesenteric arteries also respond to dopamine through specific binding sites. (Strange, "Dopamine receptors: structure and function," Prog Brain Res. 99:167–79, 1993; Strange, "New insights into dopamine receptors in the central nervous system," Neurochem. Int. 22(3):223–236, 1993.) Molecular cloning revealed that this receptor family consists of five genes, D1–D5, that modulate the activity of adenyl cyclase. The D1 and D5 dopamine receptors stimulate adenylyl cyclase activity, while the D2, D3 and D4 receptors inhibit this enzyme. (Seeman and Van-Tol, "Dopamine receptor pharmacology," Curr. Opin. Neurol.

Neurosurg. 6(4):602–608, 1993; Kebabian, "Multiple dopamine receptors and their implications in medicine," Curr. Opin. Neurol. Neurosurg. 5(4): 514–518, 1992; Kebabian, "Brain dopamine receptors: 20 years of progress," Neurochem. Res. 18(1):101–104, 1993; Sibley, et al., "Molecular neurobiology of dopaminergic receptors," Int. Rev. Neurobiol. 35:391–415, 1993.)

Dopaminergic agents and their antagonists serve to treat movement disorders, other neuropsychiatric disorders, nausea, and certain hormonal disorders.

Dopamine $D_1$ receptors are coupled to adenyl cyclase. Known Dopamine $D_1$ antagonists include SCH23390 (8-chloro-2,3,4,5-tetrahydro-3-methyl-5-phenyl-1H-3-benzazepin-7-ol hemimaleate):

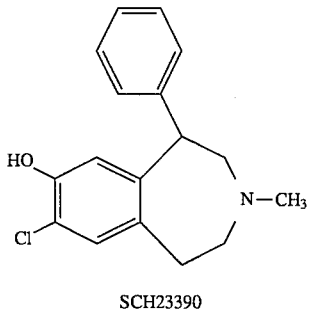

SCH23390

Dopamine D1 antagonists have demonstrated a role in the treatment of Alzheimer's disease. In the radial-arm maze test, an assay used for testing memory enhancing agents, medial cholinergic pathway lesions produce evidence of memory loss and chronic treatment with SCH23390 reversed the lesion-induced impaired performance. (McGurk et al. "Dopaminergic drugs reverse the impairment of radial-arm maze performance caused by lesions involving the cholinergic medial pathway," Neuroscience. 50(1):129–135, 1992).

Dopamine D1 receptor antagonists are also useful in the treatment of movement disorders such as Gilles de la Tourette syndrome, dystonia, and tardive dyskinesia. Dopamine D1 receptor antagonists are also useful in treating psychoses, most particularly schizophrenia.

Gilles de la Tourette syndrome, or hereditary multiple tic disorder, begins in childhood with simple tics but progresses to multiple, complex movements including respiratory and vocal tics. In 50% of patients, coprolalia, involuntary scatologic utterances, occurs. The tics and coprolalia may be severe enough to be physically and socially disabling. Gilles de la Tourette syndrome is generally treated with haloperidol, 0.5 to 40 mg/day. The dosage of haloperidol is limited by side effects such as dysphonia, parkinsonism and akathisia. Clonidine, 0.1 to 0.6 mg/day may also be effective in some patients, but is limited by the side effect of hypotension. The present invention, by potentiating the dopamine D1 receptor antagonists, permits the treatment of Gilles de la Tourette syndrome with a decreased administration of dopamine D1 receptor antagonists.

Dystonia is characterized by sustained abnormal postures and disruptions of ongoing movement resulting from alterations in muscle tone. Dystonia is generally treated with high dose anticholinergics such as trihexyphenidyl 6 to 30 mg/day, benztropine 3 to 14 mg/day, and reserpine, a dopamine depleting drug, 0.1 to 0.6 mg/day.

Tardive dyskinesia is characterized by choreiform movements of the buccal-lingual-fascial muscles, less commonly the extremeities. Rarely, focal or even generalized dystonia may be seen. Tardive dyskinesia may be caused by high doses of phenothiazines given over a long time, a common practice in young schizophrenics. Older patients, particularly women and those with brain injury, have a higher incidence of tardive dyskinesia The problem does not disappear when the drug is discontinued and resists standard treatments for movement disorders. Anticholinergics can exascerbate tardive dyskinesia. The incidence has increased with the common and prolonged use of phenothiazines. By potentiation the effect of dopamine D1 receptor antagonists administered, NER receptor activators such as TOFA, are useful in the prevention of tardive dyskinesia.

Known dopamine D1 receptor agonists include SKF 38390 (1-phenyl-7,8-dihydroxy-2,3,4,5-tetrahydro-1H-3-benzazepine):

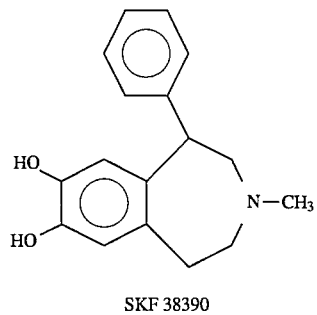

SKF 38390

Dopamine $D_1$ receptor agonists are useful in treating Parkinson's Disease.

Haloperidol is a preferential blocker of dopamine D2 receptors. Other Dopamine $D_2$ receptor modulators include dihydroergocryptine and bromocryptine.

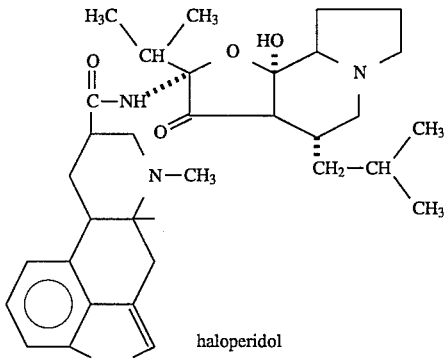

haloperidol

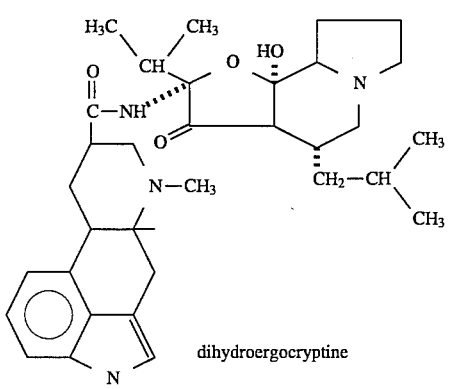

dihydroergocryptine

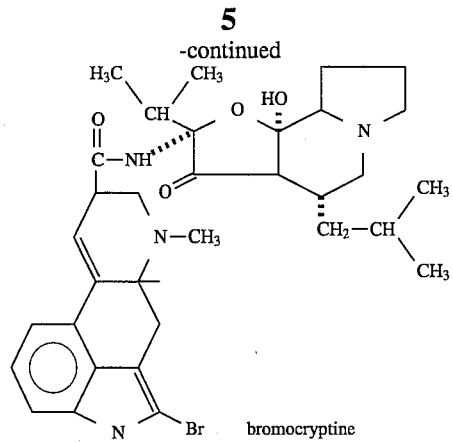

bromocryptine

The muscarinic receptors naturally bind acetylcholine.

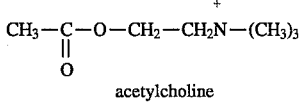

acetylcholine

The plant alkaloid muscarine also activates the muscarinic cholinergic receptors.

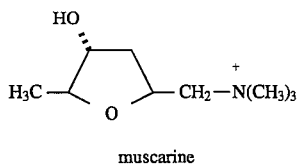

muscarine

Muscarinic receptors occur at post ganglionic parasympathetic terminals involved in gastrointestinal and ureteral peristalsis, the promotion of glandular secretion, pupillary constriction, peripheral vasodilation and reduction in heart rate. The muscarinic receptor is also a G-protein coupled receptor, and its stimulation causes an increase in cGMP. Pilocarpine is a known muscarinic agonist.

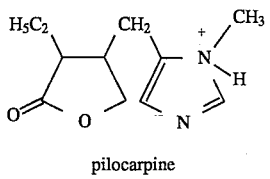

pilocarpine

Others include carbachol, metacholine, betanechol, arecoline, and oxotremorine.

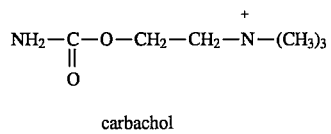

carbachol

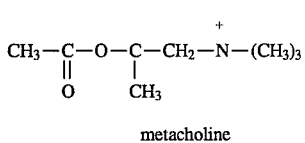

metacholine

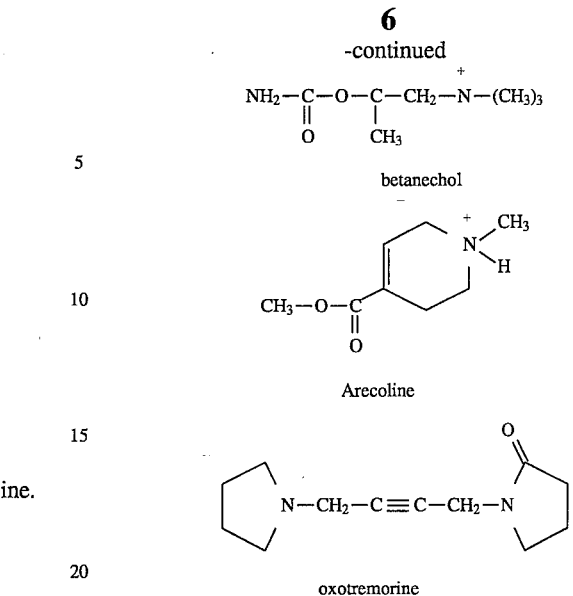

betanechol

Arecoline oxotremorine

Muscarinic agonists are useful for the treatment of ocular hypertension, particularly in glaucoma, and to stimulate the gastrointestinal tract and urinary bladder to relieve post operative atony.

NGF, nerve growth factor, is required for the development of sympathetic and sensory neurons and for neuronal viability in mature brain cells. NGF treatment induces the expression of the immediate early response gene-the orphan steroid hormone receptor Nur77. (Davis et al., "Transcriptional activation by Nur77, a growth factor inducible member of the steroid hormone receptor superfamily". Mol Endocrinol. 5(6): 854–859, 1991; Hazel et al., "Nur77 is differentially modified in PC12 cells upon membrane depolarization and growth factor treatment," Mol Cell Biol 11(6):3293–3246, 1991; Milbrandt, "Nerve growth factor induces a gene homologous to the glucocorticoid receptor gene," Neuron 1(3):183–188, 1993). Due to its role in neuronal maintenance and its ability to stimulate nerve growth, NGF is potentially important for the treatment of Alzheimer's disease. (Olson, "Reparative strategies in brain-treatment strategies based on trophic factors and cell transfer techniques," Acta Neurochirurgica 58:3–7, 1993). The potential benefit of NGF in Alzheimer's disease is also suggested by the recent demonstration of memory improvement following intracranial infusion of NGF in an Alzheimer's patient. Thus, NGF appears to be able to counteract the cholinergic deficits of Alzheimer's disease. (Seiger et al. "Intercranial infusion of purified nerve growth factor to an alzheimer patient," Behavioral Brain Research 57:255–261, 1993).

DETAILED DESCRIPTION OF THE INVENTION

One embodiment of the invention concerns human steroid hormone receptor NER, said receptor being free of other human receptor proteins.

In one class this embodiment concerns human steroid hormone receptor NER, said receptor being free of other human proteins.

Within this class, this embodiment concerns human steroid hormone receptor NER from human cells such as osteosarcoma, said receptor being free of other human proteins.

In a second class, this embodiment concerns a protein comprising the following 461 amino acid sequence (SEQ ID NO:2:) depicted from the amino to the carboxy terminus:

| | | | | | | | | | | | | | | |
|---|---|---|---|---|---|---|---|---|---|---|---|---|---|---|
| Met 1 | Ser | Ser | Pro | Thr 5 | Thr | Ser | Ser | Leu | Asp 10 | Thr | Pro | Leu | Pro | Gly 15 | Asn |
| Gly | Pro | Pro | Gln 20 | Pro | Gly | Ala | Pro | Ser 25 | Ser | Ser | Pro | Thr | Val 30 | Lys | Glu |
| Glu | Gly | Pro 35 | Glu | Pro | Trp | Pro | Gly 40 | Gly | Pro | Asp | Pro | Asp 45 | Val | Pro | Gly |
| Thr | Asp 50 | Glu | Ala | Ser | Ser 55 | Ala | Cys | Ser | Thr | Asp | Trp 60 | Val | Ile | Pro | Asp |
| Pro 65 | Glu | Glu | Glu | Pro | Glu 70 | Arg | Lys | Arg | Lys | Lys 75 | Gly | Pro | Ala | Pro | Lys 80 |
| Met | Leu | Gly | His | Glu 85 | Leu | Cys | Arg | Val | Cys 90 | Gly | Asp | Lys | Ala | Ser 95 | Gly |
| Phe | His | Tyr | Asn 100 | Val | Leu | Ser | Cys | Glu 105 | Gly | Cys | Lys | Gly | Phe 110 | Phe | Arg |
| Arg | Ser | Val 115 | Val | Arg | Gly | Gly | Ala 120 | Arg | Arg | Tyr | Ala | Cys 125 | Arg | Gly | Gly |
| Gly | Thr 130 | Cys | Gln | Met | Asp | Ala 135 | Phe | Met | Arg | Arg | Lys 140 | Cys | Gln | Gln | Cys |
| Arg 145 | Leu | Arg | Lys | Cys | Lys 150 | Glu | Ala | Gly | Met | Arg 155 | Glu | Gln | Cys | Val | Leu 160 |
| Ser | Glu | Glu | Gln | Ile 165 | Arg | Lys | Lys | Ile 170 | Arg | Lys | Gln | Gln | Gln 175 | Gln |
| Glu | Ser | Gln | Ser 180 | Gln | Ser | Gln | Ser | Pro 185 | Val | Gly | Pro | Gln | Gly 190 | Ser | Ser |
| Ser | Ser | Ala 195 | Ser | Gly | Pro | Gly | Ala 200 | Ser | Pro | Gly | Gly | Ser 205 | Glu | Ala | Gly |
| Ser | Gln 210 | Gly | Ser | Gly | Glu | Gly 215 | Glu | Gly | Val | Gln | Leu 220 | Thr | Ala | Ala | Gln |
| Glu 225 | Leu | Met | Ile | Gln | Gln 230 | Leu | Val | Ala | Ala | Gln 235 | Leu | Gln | Cys | Asn | Lys 240 |
| Arg | Ser | Phe | Ser | Asp 245 | Gln | Pro | Lys | Val | Thr 250 | Pro | Trp | Pro | Leu | Gly 255 | Ala |
| Asp | Pro | Gln | Ser 260 | Arg | Asp | Ala | Arg | Gln 265 | Gln | Arg | Phe | Ala | His 270 | Phe | Thr |
| Glu | Leu | Ala 275 | Ile | Ile | Ser | Val | Gln 280 | Glu | Ile | Val | Asp | Phe 285 | Ala | Lys | Gln |
| Val | Pro 290 | Gly | Phe | Leu | Gln | Leu 295 | Gly | Arg | Glu | Asp | Gln 300 | Ile | Ala | Leu | Leu |
| Lys 305 | Ala | Ser | Thr | Ile | Glu 310 | Ile | Met | Leu | Leu | Glu 315 | Thr | Ala | Arg | Arg | Tyr 320 |
| Asn | His | Glu | Thr | Glu 325 | Cys | Ile | Thr | Phe | Leu 330 | Lys | Asp | Phe | Thr | Tyr 335 | Ser |
| Lys | Asp | Asp | Phe 340 | His | Arg | Ala | Gly | Leu 345 | Gln | Val | Glu | Phe | Ile 350 | Asn | Pro |
| Ile | Phe | Glu 355 | Phe | Ser | Arg | Ala | Met 360 | Arg | Arg | Leu | Gly | Leu 365 | Asp | Asp | Ala |
| Glu | Tyr 360 | Ala | Leu | Leu | Ile | Ala 375 | Ile | Asn | Ile | Phe | Ser 380 | Ala | Asp | Arg | Pro |
| Asn 385 | Val | Gln | Glu | Pro | Gly 390 | Arg | Val | Glu | Ala | Leu 395 | Gln | Gln | Pro | Tyr | Val 400 |
| Glu | Ala | Leu | Leu | Ser 405 | Tyr | Thr | Arg | Ile | Lys 410 | Arg | Pro | Gln | Asp 415 | Gln | Leu |
| Arg | Phe | Pro | Arg 420 | Met | Leu | Met | Lys | Leu 425 | Val | Ser | Leu | Arg | Thr 430 | Leu | Ser |

| Ser | Val | His | Ser | Glu | Gln | Val | Phe | Ala | Leu | Arg | Leu | Gln | Asp | Lys | Lys |
|-----|-----|-----|-----|-----|-----|-----|-----|-----|-----|-----|-----|-----|-----|-----|-----|
|     |     | 435 |     |     |     |     | 440 |     |     |     |     | 445 |     |     |     |

| Leu | Pro | Pro | Leu | Leu | Ser | Glu | Ile | Trp | Asp | Val | His | Glu |
|-----|-----|-----|-----|-----|-----|-----|-----|-----|-----|-----|-----|-----|
|     | 450 |     |     |     |     | 455 |     |     |     |     | 460 |     | or a degenerate variation thereof;
the protein being free of other human receptor proteins.

A second embodiment concerns a DNA sequence encoding human steroid hormone receptor NER complementary DNA, said DNA sequence being free of other human DNA sequences.

As will be appreciated by those of skill in the art, there is a substantial amount of redundancy in the set of codons which translate specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenerate variation. Also included are mutations (exchange of individual amino acids) which one of skill in the art would expect to have no effect on functionality, such as valine for leucine, arginine for lysine and asparagine for glutamine.

One class of the second embodiment of the invention concerns the following nucleotide sequence (SEQ ID NO:1:) of complementary DNA depicted from the 5' to the 3' terminus:

An expression construct, such as a plasmid which comprises:
a) an expression vector, such as PJ3NERI, and
b) a base sequence encoding human steroid hormone receptor NER protein.

Within this class of the third embodiment, the steroid hormone receptor NER comprises the nucleotide sequence (SEQ ID NO:1:) of complementary DNA as shown above.

A second class of this third embodiment of the invention concerns a system for the transient expression of human steroid hormone receptor NER in a suitable host cell, such as a monkey kidney cell line (COS), the system comprised of a vector which expresses human steroid hormone receptor NER cDNA.

It is understood, and is readily apparent to those skilled in the art, that a wide variety of commonly used cell lines are suitable for use in the present invention. Suitable cell lines derived from various species include, but are not limited to, cell lines of human, bovine, porcine, monkey, and rodent origin, or from yeast and bacterial strains.

A fourth embodiment of the invention concerns a method of using any of the above eukaryote or prokaryote expression systems for determining the binding affinity of a test sample for steroid hormone receptor NER.

```
CAAGAAGTGG CGAAGTTACC TTTGAGGGTA TTTGAGTAGC GGCGGTGTGT CAGGGGCTAA       60
AGAGGAGGAC GAAGAAAAGC AGAGCAAGGG AACCCAGGGC AACAGGAGTA GTTCACTCCG      120
CGAGAGGCCG TCCACGAGAC CCCCGCGCGC AGGCATGAGC CCCGCCCCCC ACGCATGAGC      180
CCCGCCCCCC GCTGTTGCTT GGAGAGGGGC GGGACCTGGA GAGAGGCTGC TCCGTGACCC      240
CACCATGTCC TCTCCTACCA CGAGTTCCCT GGATACCCCC CTGCCTGGAA ATGGCCCCCC      300
TCAGCCTGGC GCCCCTTCTT CTTCACCCAC TGTAAAGGAG GAGGGTCCGG AGCCGTGGCC      360
CGGGGGTCCG GACCCTGATG TCCCAGGCAC TGATGAGGCC AGCTCAGCCT GCAGCACAGA      420
CTGGGTCATC CCAGATCCCG AAGAGGAACC AGAGCGCAAG CGAAAGAAGG GCCCAGCCCC      480
GAAGATGCTG GGCCACGAGC TTTGCCGTGT CTGTGGGGAC AAGGCCTCCG GCTTCCACTA      540
CAACGTGCTC AGCTGCGAAG GCTGCAAGGG CTTCTTCCGG CGCAGTGTGG TCCGTGGTGG      600
GGCCAGGCGC TATGCCTGCC GGGGTGGCGG AACCTGCCAG ATGGACGCTT TCATGCGGCG      660
CAAGTGCCAG CAGTGCCGGC TGCGCAAGTG CAAGGAGGCA GGGATGAGGG AGCAGTGCGT      720
CCTTTCTGAA GAACAGATCC GGAAGAAGAA GATTCGGAAA CAGCAGCAGC AGGAGTCACA      780
GTCACAGTCG CAGTCACCTG TGGGGCCGCA GGGCAGCAGC AGCTCAGCCT CTGGGCCTGG      840
GGCTTCCCCT GGTGGATCTG AGGCAGGCAG CCAGGGCTCC GGGGAAGGCG AGGGTGTCCA      900
GCTAACAGCG GCTCAAGAAC TAATGATCCA GCAGTTGGTG GCGGCCCAAC TGCAGTGCAA      960
CAAACGCTCC TTCTCCGACC AGCCCAAAGT CACGCCCTGG CCCCTGGGCG CAGACCCCCA     1020
GTCCCGAGAT GCCCGCCAGC AACGCTTTGC CCACTTCACG GAGCTGGCCA TCATCTCAGT     1080
CCAGGAGATC GTGGACTTCG CTAAGCAAGT GCCTGGTTTC CTGCAGCTGG GCCGGGAGGA     1140
CCAGATCGCC CTCCTGAAGG CATCCACTAT CGAGATCATG CTGCTAGAGA CAGCCAGGCG     1200
CTACAACCAC GAGACAGAGT GTATCACCTT CTTGAAGGAC TTCACCTACA GCAAGGACGA     1260
CTTCCACCGT GCAGGCCTGC AGGTGGAGTT CATCAACCCC ATCTTCGAGT TCTCGCGGGC     1320
CATGCGGCGG CTGGGCCTGG ACGACGCTGA GTACGCCCTG CTCATCGCCA TCAACATCTT     1380
CTCGGCCGAC CGGCCCAACG TGCAGGAGCC GGGCCGCGTG GAGGCGTTGC AGCAGCCCTA     1440
CGTGGAGGCG CTGCTGTCCT ACACGCGCAT CAAGAGGCCG CAGGACCAGC TGCGCTTCCC     1500
GCGCATGCTC ATGAAGCTGG TGAGCCTGCG CACGCTGAGC TCTGTGCACT CGGAGCAGGT     1560
CTTCGCCTTG CGGCTCCAGG ACAAGAAGCT GCCGCCTCTG CTGTCGGAGA TCTGGGACGT     1620
CCACGAGTGA GGGGCTGGCC ACCCAGCCCC ACAGCCTTGC CTGACCACCC TCCAGCAGAT     1680
AGACGCCGGC ACCCCTTCCT CTTCCTAGGG TGGAAGGGGC CCTGGGCGAG CCTGTAGACC     1740
TATCGGCTCT CATCCCTTGG GATAAGCCCC AGTCCAGGTC CAGGAGGCTC CCTCCCTGCC     1800
CAGCGAGTCT TCCAGAAGGG GTGAAAGGGT TGCAGGTCCC GACCACTGAC CCTTCCCGGC     1860
TGCCCTCCCT CCCCAGCTTA CACCTCAAGC CCAGCACGCA GCGTACCTTG AACAGAGGGA     1920
GGGGAGGACC CATGGCTCTC CCCCCCTAGC CCGGGAGACC AGGGGCCTTC CTCTTCCTCT     1980
GCTTTTATTT AATAAAAATA AAAACAGAAA AAAAAAAAAA AAAAAAAAAA                2030
```

A third embodiment of this invention concerns systems for expressing all or part of the human steroid hormone receptor NER.

One class of this third embodiment of the invention comprises:

Following the isolation of a DNA sequence encoding human steroid hormone receptor NER cDNA, a chimeric gene can be created by substituting the DNA-binding domain region in the DNA sequence encoding NER cDNA with a DNA-binding domain region taken from a DNA sequence coding for another steroid hormone receptor protein, e.g., glucocorticoid (GR) receptor protein, thyroid receptor protein, mineral corticoid receptor protein or retinoic acid receptor protein. Next, a suitable receptor-deficient host cell is transfected with: (1) the chimeric receptor gene, which is preferably carried on an expression plasmid, and (2) a reporter gene, such as the CAT gene or the firefly luciferase gene, which is also preferably carried on a plasmid. In any case, the reporter gene is functionally linked to an operative hormone response element (HRE) (either wild-type or engineered) wherein the hormone response element is capable of being activated by the DNA-binding domain used to make the chimeric receptor gene. (For example, if the chimeric receptor gene contains the DNA-binding domain region from glucocorticoid receptor coding DNA, then the HRE should be a wild-type, an engineered, or a synthetic GRE, i.e., one that can be activated by the operative portion of the DNA-binding region of a GR receptor protein.) Next, the transfected host cell is challenged with a test sample which contains one or more ligand(s) which can potentially bind with the ligand-binding domain region of the chimeric protein coded for by the chimeric gene. To determine the extent that ligands can functionally complex with the chimeric receptor protein, induction of the reporter gene is monitored by monitoring changes in the protein levels of the protein coded for by the reporter gene. (For example, if luciferase is the reporter gene, the production of luciferase is indicative of receptor-regulated gene transcription.) Finally, when a ligand(s) is found that can induce transcription of the reporter gene, it is concluded that this ligand(s) can bind to the receptor protein coded for by the initial sample DNA sequence. This conclusion can be further verified by testing the binding properties of the receptor protein, coded for by the initial sample DNA sequences, vis-a-vis the ligand(s) that induce expression of the reporter gene.

The fourth embodiment further concerns a method for determining the affinity of a test sample for activation of the steroid hormone receptor NER, the method comprising:

(a) constructing a chimeric gene by substituting portions of a DNA-binding domain region of a DNA sequence encoding human steroid hormone receptor NER cDNA with operative portions of a DNA-binding domain region from a known ligand-responsive receptor protein;

(b) introducing into a suitable receptor-deficient host cell:
  (i) the chimeric gene from step (a), and
  (ii) a reporter gene functionally linked to an operative hormone response element wherein the hormone response element is capable of being activated by the DNA-binding domain region of the receptor protein encoded by the chimeric gene of step (a);

(c) challenging the transfected host cell from step (b) with the test sample to be evaluated for ligand-binding activity with the chimeric receptor protein encoded by the chimeric gene of step (a);

(d) assaying induction of the reporter gene by monitoring changes in the protein levels of the protein coded for by the reporter gene.

One class of this embodiment concerns a method of using a monkey kidney cell line (COS) as the suitable receptor-deficient host cell. In addition, the COS host cell line may be transfected with a plasmid, the plasmid comprising:

(a) an expression vector, such as PJ3NERI, and
(b) the base sequence encoding human steroid hormone receptor NER protein.

The aforementioned fourth embodiment is further useful for identifying compounds, such as TOFA, which compounds potentiate the effects of ligands for other receptors, such as the Dopamine D1 receptor and the muscarinic receptor. This embodiment is also useful in identifying ligands for new hormone systems which regulate bodily function. Another use of the aforesaid embodiment is potentiating the activity of a modulator of a G-protein coupled receptor which comprises administering a compound which activates the NER receptor, most particularly in a subject in need thereof.

Yet another class of this embodiment of the present invention comprises ligand dependent screening assays for assessing a compound or mixture of compounds to determine whether the compound (or any one of the compounds) modulate the NER receptor. Ligand dependent screening assays are performed by co-expressing the NER receptor and a reporter gene in which the transcription is under the control of the NER receptor. Such a reporter gene can be the MMTV-luciferase reporter gene in which the MMTV promoter is modified to be under the control of the NER receptor. The plasmids containing cDNA for the NER steroid hormone receptor and the appropriate reporter gene can be transfected in to COS or other suitable cells. Ligands or extracts are added after the transfection and 18 to 48 hours later, the cells are washed, cell extracts are prepared and assayed for luciferase activity. In some experiments, transfection is performed by batch mode in large tissue culture dishes. After 18 hours, the cells are washed and seeded into multi-well plates. After cell settling, the ligands are added and luciferase activities are tested one or two days later. All compounds or extracts are dried and dissolved in their appropriate solvent such as ethanol or DMSO as 100–1000 fold concentrated stock solutions.

In overview, the present invention describes methods to isolate the human steroid hormone receptor NER complementary DNA (cDNA) without prior knowledge of its protein sequence or gene sequence. Polymerase chain reaction (PCR) technique was utilized for the isolation of human steroid hormone receptor NER cDNA.

The complete sequence of the human steroid hormone receptor NER cDNA was determined, and its encoded protein sequence was deduced. Among other things, such sequence information is useful in the process of developing novel steroid hormone agonists and antagonists.

An expression system was used to express the cloned human steroid hormone receptor NER cDNA. The COS (a monkey kidney cell line) expression system can be used to measure the ligand binding properties of human steroid hormone receptor NER.

Assay protocols use the heterologously expressed human steroid hormone receptor NER for determination of the activation of steroid hormone receptor NER by antagonists.

The present invention generally relates to a new member of the steroid hormone receptor superfamily. The amino acid sequence deduced from the DNA sequence (Bases 245 to 1027.) shows the characteristic features of both the DNA and the ligand binding domains of this family of receptors. Sequence analysis predicted a protein of 461 amino acids which includes the conserved amino acid residues characteristic of the DNA and ligand-binding domains of nuclear receptors.

This invention relates to NER, a new member of the steroid receptor-like gene family which was isolated from a human bone cell cDNA library. NER codes for a polypeptide of 461 amino acids which contains the conserved sequences of the DNA and ligand binding domains of typical steroid receptors. The best homology is shared with the different retinoic acid receptors: $\alpha$, $\beta$ & $\gamma$, 55% at the DNA $\alpha$, $\gamma$ binding domain and 38–40% at the ligand binding domain. A single transcript of 2.3 kb was detected in all cells and tissues tested. We tested the potential of these constructs to mediate ligand dependent transcription activation of reporter genes.

The nuclear receptor-gene family is expanding in size, as new members are constantly identified. Here we report the cloning of a new sequence from human osteosarcoma cells. This gene, named NER, codes for a polypeptide of 461 amino acids and contains the conserved sequences typical of both the DNA and the ligand binding domains. The amino terminus of the predicted protein contains a high number of proline and serine residues which might introduce a highly stabilized and complexed secondary structure. A high number of proline residues was also found in other nuclear receptor and other molecules with transcriptional activity such as CTf/N1, fos, jun. p53, OCT-2 and SRF (Mitchell & Tjian, Science, 245, pp. 371–378 (1989); Mermod et al., 1989).

The size of the deduced protein and the spatial distribution of the different domains resemble the arrangement found in the thyroid, vitamin D and retinoic acid-receptor subgroup (Lazar et al., Proc Natl. Acad. Sci. 86, pp. 7771–7774, 1989). The sequence homology at the predicted ligand binding domain ranges between 33–40% identity with the members of this subgroup, while homologies lower than 25% were measured when the ligand binding domain was compared to the corresponding domain of the steroid receptor subgroup which includes the estrogen, glucocorticoid, androgen and progesterone. As mentioned above, the highest homology of the ligand binding domain was the retinoic acid receptors. This homology, 40% with retinoic acid RAR2 is much lower than homologies of 79% and over which are found between RARα, RARβ, RARγ. The degree of sequence similarity, however, is not always indicative of the nature of the ligand as evident from the recently discovered new form of retinoic acid receptor, RXR which shared only a 27% identity with the other retinoic acid receptors (Oro et al., Nature, 347, pp. 298–301, 1990). It is thus impossible to assign or to exclude any of the known ligands based on sequence homology considerations. The homology at the DNA binding domain is around 50% with most other nuclear receptors. The highest degrees of homology were measured with estrogen and with retinoic acid receptors, 56%, and 53–55% respectively. However, these levels were only marginally higher than the homologies with the other receptors. It is worth noting that the homology shared between the different retinoic acid receptors (types α, β and γ) at this domain are higher than 95%. And even the homology of RXR to the other retinoic acid receptors at this region exceeds 60%.

Although cloned from an osteoblastic cell line, the mRNA for NER is widely distributed in different tissues and in all the tested cell lines.

To simplify the search for the elusive ligand, we constructed a hybrid receptor gene comprising the DNA binding domain of estrogen receptor linked to the ligand binding domain of the NER gene. Such strategy was proven successful in the identification of ligands for the PPAR receptor. Issenmann and Green, Nature, 347, pp. 645–649 (1990).

To search for putative ligands for the NER receptor, the chimeric receptor GR/NER was prepared. This chimeric receptor is capable of exhibiting ligand dependent activation of transcription of a heterologous responsive DNA sequence. Chimeric receptors were prepared in which the amino terminal portion of the mouse glucocorticoid receptor (mGR) that includes the DNA binding domain was fused to the putative ligand binding domains of the nuclear receptor NER to form the respective chimeric receptor GR/NER. The cDNA sequences coding for amino acid residues $Arg^{155}$ and $Glu^{156}$ of the hNER receptor (Shinar et al., NER, a new member of a gene family encoding the steroid hormone nuclear receptor; GENE (in press) were convened to the Xho I restriction site, which site was later used for the ligation to the GR cDNA sequences that coded for the DNA binding domain. Thus, the amino acid residues $Arg^{155}$ and $Glu^{156}$ of the NER receptor were convened to amino acid residues $Ser^{155}$ and $His^{156}$.

The chimera was employed in ligand dependent transactivation assays with the reporter gene MMTV-luciferase, in which the luciferase cDNA is transcribed under the control of the MMTV promoter.

TOFA was identified as a ligand of the NER receptor via directed screening of compounds topologically similar to fatty acids from the Merck Chemical Collection. The compounds were selected from the Merck Chemical Structure Database by using Merck's topological similarity (TOPOSIM) program that is the result of unpublished work by Simon Kearsley which is based on the similarity descriptors developed at Lederle Laboratories (Raymond E. Charhart, Dennis H. Smith, R. Venkataraghavan, J. Chem. Inf. Comp. Science, 1985, 25:64–73) but which includes additional descriptors such as partial charge. About 250 compounds were selected for testing in the transactivation assays. TOFA stimulated the expression mediated by the GR/NER, GR/NUC and GR/PPAR hybrid receptors, in a dose dependent manner. In contrast to TOFA, the ligands Wy14643 and oleic acid maintained their expected receptor specificity, and activated expression mediated by GR/PPAR and GR/NUC but not by the GR/NER receptors. However, TOFA did not act as a general stimulator of transcription since it did not stimulate expression of the MMTV-luciferase reporter gene after co-transfection of the native NUCI and glucocorticoid receptors. The specific action of TOFA was further demonstrated by the fact that TOFA did not stimulate the expression of luciferase in cells transfected only with the MMTV-luciferase reporter gene, or with a reporter gene in which the expression was under the control of the early promoter of SV40.

These ligand dependent transcription assays and the binding assays to the NER receptor may be used to identify additional compounds, including those that are more potent than TOFA or have better selectivity toward activation of G protein-coupled receptors.

TOFA was found to activate transcription mediated by the ligand binding domain of the unrelated NUC and NER receptors. It is thus possible that TOFA may be interacting indirectly with these receptors in a ligand independent fashion akin to the interaction of dopamine with the COUP-TF receptor (Power et al., Dopamine activation of an orphan of the steroid receptor superfamily, Science 252(5012): 1546–1548, 1991; Power et al., Dopaminergic and ligand-independent activation of steroid hormone receptors, Science 254(5038): 1636–1639, 1991; Power et al., New insights into activation of the steroid hormone receptor superfamily, Trends Pharmacol. Sci. 13(8): 318–323, 1992). To gain information for the interaction between TOFA and the D1 dopaminergic system, we tested the in vitro and in vivo interaction between teh dopamine receptor agonist dopamine, the dopamine D1 receptor antagonist SCH23390, and TOFA in vivo and in vitro. Contrary to the reports disclosed by Power et al. (supra) that the treatment of CV1 cells with dopamine activates transcription mediated by steroid hormone receptors, treatment of CV1 cells with dopamine did not stimulate the transcription mediated by GR/NER. Moveover, in COS cells that do not express the D1 dopamine receptor, TOFA activated the transcription mediated by the GR/NER chimeric receptor. Furthermore, dopamine suppressed transcription mediated by GR/NER in CV1 cells but not in COS celss. Treatment withsCH23390 increased transcirption and alleviated the suppression of transcription induced by dopamine. These results indicate that, although there is cross talk between TOFA and the dopaminergic system, TOFA activates the receptors via a different molecular mechanism than that suggested for the stimulation of steroid hormone receptors by dopamine. To gain information for the interaction between TOFA and the $D_1$ dopaminergic system in vivo, we tested the in vivo interaction between the dopamine receptor antagonist, SCH23390 and TOFA using the catalepsy induced by the $D_1$ antagonists in rats. Pretreatment with TOFA markedly increased the SCH23390 catalepsy by at least 25 fold. The catalepsy induced by pilocarpine, an agonist of the muscarinic cholinergic receptor was potentiated by about 3 fold by TOFA pretreatment. However, the catalepsy induced by the $D_2$ dopamine receptor antagonist haloperidol was unaffected by TOFA pretreatment.

This invention also relates to a method of finding potentiators of receptors, particularly potentiators of dopamine D1 receptor antagonists and of the muscarinic receptor. This method employs a screening procedure using the novel recombinant human steroid hormone receptor, NER.

The ligand screening assay used in the present method is described below:

Ligand dependent transcription screening assays are performed by co-expressing the NER receptor and a reporter gene in which the transcription is under the control of the NER receptor. Such a reporter gene is preferably the MMTV-luciferase reporter gene in which the MMTV promoter is modified to be under the control of the NER receptor. The plasmids containing cDNA for the NER steroid hormone receptor and the appropriate reporter gene are transfected into COS or other suitable cells. Ligands or extracts are added after the transfection and 18 to 48 hours later, the cells are washed, cell extracts are prepared and assayed for luciferase activity. Alternatively, transfection may be performed by batch mode in large tissue culture dishes. After 18 hours, cells are washed and seeded into multi-well plates. After cell settling, the ligands are added and luciferase activities are tested one or two days later. All compounds or extracts are dried and dissolved in their appropriate solvent such as ethanol or DMSO as 100–1000-fold concentrated stock solutions.

Further, this invention relates to the use of TOFA (5-(tetradecyloxy)-2-furan carboxylic acid), and pharmaceutically acceptable salts and esters thereof as a potentiator of inhibition of the dopamine D1 receptor and of the muscarinic receptor. TOFA was found through the above screening procedure employing NER. TOFA activates NER and is a potentiator of ligands for other receptors. However, TOFA has no independent effect on the receptors whose ligands are potentiated by TOFA.

TOFA appears to act through a novel mechanism of interaction with cell surface receptor mechanisms via their intracellular signaling pathways. The use of the potentiator TOFA presents clear clinical advantages, since by circumventing direct effects at the neurotransmitter receptors, alteration to receptor up and down regulations which often compromise the action of direct receptor-active drugs is avoided.

TOFA is particularly useful in the treatment of diseases for which the dopamine D1 antagonist SCH23390 is useful. For example, SCH23390 prevents the addictive properties of cocaine and may be useful in protecting or preventing the toxic effects which result from an overdose of cocaine, amphetamines or other CNS stimulants. (Lomax, and Daniel, "Cocaine and body temperature in the rat: effect of dopamine D1 antagonists", Proc. West Pharmacol. Soc. 34:5–9, 1991; and Witkin et al., "Interaction of haloperidol and SCH23390 with cocaine and dopamine receptor subtype-selective agonists on schedule-controlled behavior of squirrel monkeys", Psychopharmacology Berl. 104(4):452–431, 1991.) Further, TOFA may also be useful in potentiating the effects of SCH23390 in the treatment of schizophrenia and movement disorders including those which develop during treatment with antipsychotic drugs. In addition, TOFA is useful in potentiating the effects of SCH23390 in preventing the development of intraocular pressure induced by dopamine agonists in hydrodynamic disorders of the eye (see, Virno et al., "Dopamine, dopaminergic drugs and ocular hypertension", Int. Ophthalmol. 16(4–5):349–353, 1992), and in patients with an increase in intracranial pressure (see Boyson and Alexander, "Net Production of cerebrospinal fluid is decreased by SCH22390", Ann. Neurol. 27(6):631–635, 1990).

TOFA is also useful in potentiating the effects of SCH22390 in the treatment of Alzheimer's disease.

Further, since TOFA markedly potentiates the differentiation effect of NGF in PC12 cells and potentiates the in vivo effect of the cholinergic receptor stimulant (pilocarpine), TOFA may also be beneficially employed in treating memory disorders associated with cholinergic deficiency—both those associated with normal aging and in age-related diseases such as Alzheimer's disease.

Although TOFA is known to be a potent inhibitor of fatty acid synthesis, it is unlikely that this action is the shared mechanism through which TOFA activates these receptors. Cerulenin, another compound which is a potent inhibitor of fatty acid synthesis, Kawaguchia, A., et al. *J. Biochem.* Tokyo, (1982) 92, 7–12, does not mimic the potentiating effects of TOFA, adding further evidence to demonstrate that inhibition of fatty acid synthesis per se is not responsible for the activation of the chimeric receptors and the cross talk with the dopamine receptor signaling pathway.

In summary, we have identified a new member of the steroid hormone receptor superfamily. The identification of these functions may provide us with an insight into a novel hormonal regulated system.

The pharmaceutically acceptable salts of the compound of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting the free acid with a suitable organic or inorganic base.

Esters of TOFA may be prepared by dissolving the TOFA in a dry organic solvent, preferably tetrahydrofuran (THF) at 0°–30° C. and treating with the appropriately substituted isourea for 8–24 hours, cooling to −15° C. and filtering the urea. The filtrate is concentrated under reduced pressure to yield the desired ester. Especially suitable esters of the present invention include:

(a) $C_{1-5}$ alkyl, or (b) $C_{1-5}$ alkyl substituted with
  (i) phenyl, or
  (ii) phenyl substituted with methyl, methoxy, Cl, Br, I, F or hydroxy;

however, other pharmaceutically acceptable esters may be employed.

Activators of NER, such as TOFA, can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the activator of NER is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the activator of NER required to potentiate the effects of the dopamine D1 antagonist or the muscarinic agonist, or to stimulate the production and effects of NGF.

Oral dosages of the present invention, when used for the indicated effects, will range between about 0.01 to 100 mg/kg of the NER activator, preferably 0.1 to 50 mg per day. The compositions are preferably provided in the form of tablets containing 0.5, 1.0, 2.5, 5.0, 10.0, 15.0, 25.0 and 50.0 mg of active ingredient. Advantageously, TOFA may be administered in a single daily dose or less frequently, or the total daily dosage may be administered in divided doses of two, three or four times daily. Furthermore, TOFA can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

In the methods of the present invention, TOFA can form the active potentiating ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, nontoxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Activators of NER such as TOFA can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines.

Activators of NER such as TOFA may also be delivered by the use of monoclonal antibodies as individual carriers to which the compound molecules are coupled. TOFA may also be coupled with soluble polymers as targetable drug carriers. Such polymers can include polyvinylpyrrolidone, pyran copolymer, polyhydroxypropylmethacrylamidephenol, polyhydroxyethylaspanamidephenol, or polyethyleneoxidepolylysine substituted with palmitoyl residues. Furthermore, the TOFA may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Most preferably, activators of NER such as TOFA are administered in combination with compounds which themselves exhibit agonism or antagonism of G-coupled receptors, such as: pilocarpine, SCH23390, dihydroergocryptine, bromocryptine, metacholine, carbachol, betanechol, arecoline and oxotremorine, most preferably pilocarpine and SCH23390.

As used herein, the term "administration" refers to both concurrent and sequential administration of the NER activator and the potentiated agents. Examples of such potentiated agents would include, but are not limited to, dopamine D1 receptor antagonists and muscarinic receptor agonists. Illustrative of such dopamine D1 receptor antagonists are: SCH23390, dihydroergocryptine, and bromocryptine, and illustrative of such muscarinic receptor agonists are: pilocarpine, metacholine, carbachol, betanechol, arecoline and oxotremorine. Dosages of dopamine D1 receptor antagonists range from 0.001 to 20 mg/kg, most preferably 0.1 to 5 mg/kg. Dosages of muscarinic receptor agonists may be administered topically for the treatment of elevated intraocular pressure in a 1 to 2% solution, or they may be administered orally or parenterally in dosage ranges from 0.001 to 20 mg/kg, most preferably 0.1 to 5 mg/kg.

As used herein, "steroid hormone receptor superfamily" refers to the class of related receptors comprised of glucocorticoid, mineralocorticoid, progesterone, estrogen, estrogen-related, vitamin $D_3$, thyroid, v-erb-A, retinoic acid and E75 (Drosophilia) receptors. As used herein "steroid hormone receptor" refers to members within the steroid hormone receptor superfamily.

As used herein, "ligand" means an inducer, such as a hormone or growth substance. Inside a cell, the ligand binds to a receptor protein, thereby creating a ligand-receptor complex, which in turn can bind to an appropriate hormone response element. Single ligands may have multiple receptors.

As used herein, the term "potentiator" means an agent or mechanism which enhances the actions of a second agent or mechanism. The term "potentiating amount" refers to the amount of potentiatior that must be administered in order to produce the potentiating effect in a subject.

The term "pharmacologically effective amount" shall mean that amount of a drug or pharmaceutical agent that will elicit the biological or medical response of a tissue, system, animal or human that is being sought by a researcher or clinician.

As used herein, "expression construct" refers to a plasmid or vector comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. "Recombinant expression system" means a combination of an expression construct and a suitable host microorganism. As used herein, the term "receptor" refers to a binding or recognition site with a specific molecular configuration on a cell surface or within a cell structure, which causes a physiologic response upon stimulation by a neurotransmitter or other chemical, including a drug or toxin.

As used herein, the term "G-coupled receptor" refers to a receptor that when activated is coupled to a membrane protein which binds GTP (G-protein) on its cytoplasmic surface and couples the activated receptor with adenylate cyclase. "Adenyl cyclase coupled receptor" refers to a receptor that when activated directly activates the enzyme adenylate cyclase.

The following examples are given for the purpose of illustrating the present invention and shall not be construed as being limitations on the scope or spirit of the instant invention.

EXAMPLE 1

Primers Design

Degenerate DNA primers were designed to recognize the consensus sequences of the DNA and ligand binding domains of a typical nuclear receptor. The 5' primer ES11, (Seq. ID. No. 3) was degenerate oligomer 5' TGT-GAGGGCTGCAA(G/A)G(C/G)C, based on the conserved amino acids CEGCKA(G) of the DNA binding domain. A second 5' primer, ES12, (Seq. ID. No. 4) TGTGAGGGCTGCAA(G/A)G(C/G)CTTCTTC contains six additional nucleotides at its 3'-end corresponding to two conserved phenylalanine residues following the CEGCKA(G) sequence. The antisense primer, ES 15 (Seq. ID. No. 5) AA(G)A(C,T,G)CCA(C,T,G)GGIAIIIIC(T)TTT(A,G, C)GC(G)TT, was designed to complement the semiconserved amino acid sequence FAKxxPGF of the ligand binding domain of a typical receptor. The nucleotides corresponding to the nonconserved amino acids (xx) were substituted with inosine (I) residues.

PCR Amplification

To use the polymerase chain reaction (PCR) method, degenerate oligonucleotides were synthesized according to the amino acid sequence of two conserved segments shared by members of the nuclear receptor superfamily (R. M. Evans, Science 240:899–895 (1988)). The 5' end primers, ES11 and ES 12, were designed according to a segment of the DNA binding domain. The primer at the 3' end, ES 15, was prepared according to a conserved amino acid sequence in the ligand binding domain of the retinoid receptor subfamily and the vitamin D receptor. Since this conserved region contains two nonconserved amino acid residues, inosine nucleotides were used as part of this primer. Human cDNA prepared from mRNA of osteosarcoma cells SAOS-2/B10, amplified with the primers ES11 and ES15, yielded multiple DNA fragments with various sizes after the first round of amplification. A portion of the reaction was subjected to a second round of amplification using the nested primer ES12 and the same 3' end primer ES15.

A random primed cDNA library was prepared from 2 µg total RNA isolated from the osteosarcoma SAOS-2/B10 cells by the Moloney reverse transcriptase enzyme RTH according to the manufacturer recommendations (Bethesda Research Laboratories). The cDNA reaction (25 µL) was diluted into 300 mL water and heat denatured at 95° C. for 5 minutes and quickly chilled on ice. The cDNA (2.5 µL) and the first primer pair, ES11 and ES15 (0.5 µM each) were employed in the amplification reaction with the amplitaq kit and the DNA thermal cycler (Perkin-Elmer-Cetus).

Primer ES11 has the following sequence (SEQ ID NO:3:):

CGAATTCTGT GAGGGCTGCA ARGSC    25 wherein:

R represents A or G; and

S represents C or G;

and Primer ES15 has the following sequence (SEQ ID NO:5:):

GGAATTCRAA NCCNGGNANN NNYTTNGCRA A    31 wherein:

N (at the 11, 14 & 26 positions) represents A or C or G or T; N (at the 17, 19, 20, 21 & 22 positions) represent inosine; R represents A or G; S represents C or G; and Y represents C or T.

The following amplification cycles were conducted: denaturation at 94° C., 1.5 minutes; annealing at 65° C., 3 minutes; extension at 72° C., 5 minutes for 3 cycles; denaturing at 94° C., 1 minute; annealing at 60° C., 3 minutes; extension at 72° C., 5 minutes for 15 cycles; and denaturing at 94° C., 1 minute; annealing at 57° C., 3 minutes; extension at 72° C., 5 minutes for 20 cycles.

After completion of the first round of amplification, 5 µL of the reaction was added to an amplification reaction buffer containing a second set of primers: a partially nested oligomer ES12 and the same 3' end primer ES15 (0.5 µM each).

Primer ES12 has the following sequence (SEQ D NO:4:):

CGAATTCTGT GAGGGCTGCA ARGSCTTCTT C    31 wherein:

R represents A or G; and

S represents C or G.

The second round of amplification was performed with the same program used for the first amplification cycles. The amplification products were separated on 5% polyacrylamide gel and stained by ethidium bromide. The DNA products were isolated from the gel, phosphorylated by T4 polynucleotide kinase and cloned into PUC 18 vector by blunt end ligation. Clones were identified by digestion of plasmid DNA with PvuII enzyme. The DNA insert was analyzed by double-stranded DNA sequencing by the dideoxy termination method using sequenase enzyme kit (United States Biochemicals).

This amplification produced two major DNA fragments of 270 bp and 320, respectively.

EXAMPLE 2

Cloning and Sequencing of cDNA

The fragments from PCR amplification were cloned into plasmids and sequenced. The amino acid residues predicted by the DNA sequences, indicated that both DNA fragments may code for genuine and novel receptors belonging to the steroid hormone superfamily. To obtain the complete cDNA clone the amplified cDNA fragment of 270 bp NER was used for the screening of a human osteosarcoma SAOS-2/B10 cells cDNA library. All the highly positive clones were identical and matched the sequence for the amplified NER DNA fragment.

A human oligo-dT cDNA library was constructed RNA isolated from osteosarcoma SAOS-2/B10 cells using the Lambda Librarian cloning kit (Invitrogen Corp.). Several positive clones were identified by plaque screening with the [$^{32}$P] labeled DNA probe of the cloned amplified product (NER). The hybridization conditions were as described by A. Schmidt, et al., *J Biol Chem* 259:7411–7415 (1984). The cDNA inserts were cloned into EcoRI site of the cloning vector PUC18. The complete DNA sequence of both strands was determined by the dideoxy sequencing method using a series of oligonucleotides synthesized as the DNA sequence data became available.

Cloning of NER

The amplification of the cDNA prepared from the RNA of Saos-2/B10 osteoblastic cell line with the ES11 and ES15 primers yielded multiple fragments after 40 rounds of amplification. Five percent of the first amplification reaction were subjected to additional 30 rounds of amplication with ES12 and ES15 oligomers. Primer ES12 that replaces ES11 is six nucleotides longer and codes for two conserved phenylalanine residues at the 3'-end, thus introduces an additional level of specificity to the amplification reaction. The second amplification step resulted in the elimination of all but two DNA fragments. The two fragments; nuc-I, 320 bp, and Ner, 270 bp, were subcloned and sequenced. Sequence analysis revealed that both DNA fragments resemble the typical DNA binding domain of steroid hormone receptor genes, but were not identical to any of the known sequences.

Surprisingly, none of the two fragments contained sequences of the ligand binding domain as could be predicted by the use of the ES15 primer derived from that region. It was later realized that the 5' ES12 oligomer primed the reaction at both directions although it shared only 53% homology with that sequence.

In order to obtain full length cDNA clone for the novel putative nuclear receptor NER, we screened a cDNA library from the Saos-2/B10 cells with the NER amplified DNA fragment. Several clones were identified and cloned into pUC18 vectors. One of the largest clones, nuc-2-103 of 2 kb was thoroughly analyzed and the nucleotide sequence and the predicted amino acid sequence were determined.

Sequencing of the NER clone revealed a long open reading frame coding for a polypeptide of 461 amino acids. The deduced protein resembles in its structure a typical steroid-like receptor. At position 87–154, a putative "double zinc finger" structure which can serve as the DNA binding domain was identified. Amino acid sequences that characterize the ligand binding domain were located toward the carboxy terminus of the protein and were spaced like in the thyroid or retinoic acid receptors. Comparing the sequence of the deduced protein with other known receptor sequences revealed that the DNA binding domain shared 50–56% homology with all the steroid-like receptors. Highest scores at this domain were: 56% for the estrogen receptor, 55% for the retinoic acid gamma receptor and mineralcorticoid receptor and 54% for retinoic acid A and glucocorticoid receptors. The ligand binding domain which is less conserved showed highest homology levels of 38–40% with the 3 types of retinoic acid receptors, RARα, RARβ and RARγ 38% with vitamin D receptor and 33% with thyroid hormone receptor. The homology to the ligand binding domains of estrogen, androgen, glucocorticoid and mineralocorticoid at this domain was significantly lower. The RXR retinoic acid receptor type X showed an intermediate value of 28% homology at this domain.

It is noteworthy that the amino acid terminus of NER (amino acids 1–87) contains high number of 17 proline residues and 10 serines.

EXAMPLE 3

Northern Blot Analysis

RNA from various tissues or the listed cell lines were prepared by using guanidine thiocyanate or by the guanidine hydrochloride method (G. G. A. Nemeth, et al., *Anal Biochem* 183:301–304 (1989); J. M. Chirgwin, et al., *Biochemistry*, 18:5294–5299 (1979)). RNA samples were analyzed by formaldehyde agarose gel electrophoresis as described by (K. M. Rosen, et al., *Focus* 12:23–24 (1990)). The RNA was transferred by blotting to N-Hybond (Amersham Corp.), and hybridized with $^{32}$P-labeled cDNA of NER as described by (A. Schmidt, et al., *J Biol Chem* 259:7411–7415 (1984); K. M. Rosen, et al., *Focus* 12:23–24 (1990)).

Total RNA was extracted from rat or baboon tissues and processed for electrophoresis and blot hybridization with $^{32}$p labeled probe of Ner-I by conventional methods as described by Fritsch et al., (1989).

Analysis of RNA from the osteoblastic Saos-2/B10 cells with the NER labeled DNA probe revealed a single transcript of approximate 2.3 kb. Similar RNA transcripts were detected in all cell lines tested. No apparent variations in size of the mRNA molecules could be observed between RNAs isolated from different species. Tissue distribution of the NER gene expression was examined by Northern hybridization. NER RNA transcripts were detected in all the rat tissues or cells which were tested. Similar results were obtained with RNA isolated from tissues of adult baboons.

Screening the Saos-2/B10 cDNA library with the labeled amplified DNA fragment encoding part of the putative novel nuclear receptor NER resulted in several positive cDNA clones. Sequence analysis of the positive clones revealed that in addition to the expected full length cDNA clone for NER receptor we obtained two clones in which the DNA sequences differed from the expected NER putative receptor. The sequence of one clone, named pE1001, matched the sequence of the known retinoic acid receptor type alpha (RARα), (Giguere et al., *Nature* 331, pp. 91–94, 1987). Sequence analysis of the second clone (pE1005), revealed the characteristics of a novel nuclear receptor published and characterized as a novel retinoic acid receptor X, (RXRα) (Mangelsdorf et al., *Nature* 345, pp. 224–229 1990). Thus, these results illustrate that the cDNA for NER receptor can be utilized as an assay tool to identify known and novel members of the class of steroid hormone nuclear receptors.

EXAMPLE 4

Activation of GR/NER, GR/NUC and GR/PPAR Hybrid Receptors by TOFA

To identify the putative ligand for NER receptor, the potential of NER to induce transcription of a reporter gene which contains inducible hormone responsive elements was examined. Several responsive elements were tested; the thyroid/retinoic acid, estrogen, vitamin D and the glucocorticoid/progesterone elements. Transfection experiments in CV-1 and L cells, revealed no ligand-dependent induction of the CAT reporter gene. To facilitate the search for a ligand, hybrid receptor molecules were constructed.

The ligand dependent transcription assays were as described below:

Similar hybrid receptors GR/NER, GR/NUC and GR/PPAR, in identical expression plasmid backgrounds were prepared essentially as described for the construction of the GR/mPPAR and GR/NUC chimeric receptors in Schmidt et al., "Identification of a new member of the steroid hormone receptor superfamily that is activated by a peroxisome proliferator and fatty acids," Mol. Endocrinol., 6(10):1634–41, 1992, and in Boie et al., "Enantioselective activation of the peroxisome proliferator-activated receptor", J. Biol. Chem. 268(8):5530–4, 1993.

Briefly, the amino terminal portion of the mouse glucocorticoid receptor (mGR), that includes the DNA binding domain was fused to the putative ligand binding domains of the nuclear receptor NER, hNUC-I (Schmidt et al., 1992), mPPAR (Issenmann and Green, 1990) to form the respective chimeric receptors GR/NER, GR/NUC and GR/PPAR. The GR/NER chimeric receptor was constructed as described for the GR/NUC and GR/PPAR hybrid receptors (Schmidt et al., 1992; Boie et al). The cDNA sequences coding for amino acids $Arg^{155}$ and $Glu^{156}$ of the NER receptor were converted to the Xho I restriction site, that was later used for the ligation to the GR cDNA sequences that coded for the DNA binding domain. Thus, converting amino acid residues $Arg^{155}$ and $Glu^{156}$ of NER receptor to amino acid residues $Ser^{155}$ and $His^{156}$.

The cDNA of the human NUCI receptor (pJ3NUCI) and the native mouse glucocorticoid receptor (pSV2WREC) were expressed under the control of SV40 based expression vectors (Schmidt et al., 1992; Boie et al., 1993). The reporter gene was the plasmid pJA358 in which the expression of firefly luciferase is regulated by two tandem repeats of the glucocorticoid hormone response element (GRE) linked to the MMTV promoter (Boie et al., 1993).

Transient transfection of COS and CV1 cells was performed as described (Schmidt 1992). Cells were plated ($1.5 \times 10^5$ in 1 mL) into 12 well dishes in phenol red-free medium supplemented with activated charcoal treated fetal calf serum. The next day 0.12 mL of DNA 10 µg/ml (5 µg receptor DNA and 5 µg reporter plasmid), as a calcium phosphate precipitate, was added to the cells. Ligands were added to the cells 30 minutes after transfection. The next day (18 hours), the cells were washed and fresh ligands added. Twenty-four hours later, cell extracts were prepared and assayed for luciferase enzyme activity using the luciferase assay system (Promega Madison, Wis.). Each transfection was performed in triplicate and the luciferase activity of each sample measured in duplicate using the AutoClinilumat (Berthold Nashua, N.H.).

The transfected cells were treated with TOFA at 2 µM, 10 µM, 20 µM, and 50 µM and oleic acid at 50 µM, and 300 µM. The results are depicted in Table 1, below.

TABLE 1

Activation of GR/NUC, GR/PPAR, GR/NER, NUC-I and GR Receptors by TOFA

| Treatment | µM | GR/NER | GR/NUC | GR/PPAR | NUC-I | GR |
|---|---|---|---|---|---|---|
| Control | 0 | 1.00 ± 0.13 | 1.00 ± 0.09 | 1.00 ± 0.19 | 1.00 ± 0.40 | 1.00 ± 0.17 |
| TOFA | 2 | 2.35 ± 0.09 | 1.95 ± 0.14 | 2.89 ± 0.13 | 0.83 ± 0.12 | 1.02 ± 0.40 |
| TOFA | 10 | 3.66 ± 0.40 | 2.85 ± 0.20 | 4.08 ± 0.10 | 0.94 ± 0.08 | 0.80 ± 0.14 |
| TOFA | 20 | 4.82 ± 0.28 | ND | 5.75 ± 0.14 | ND | ND |
| TOFA | 50 | ND | 3.19 ± 0.20 | ND | 1.27 ± 0.06 | 0.91 ± 0.30 |
| Oleic Acid | 50 | 0.90 ± 0.13 | ND | 2.87 ± 0.2 | ND | ND |
| Oleic Acid | 150 | ND | 3.42 ± 0.28 | ND | 0.55 ± 0.08 | 0.44 ± 0.17 |
| Oleic Acid | 300 | 0.73 ± 0.21 | ND | 14.69 ± 0.06 | | |
| WY14643 | 100 | 0.57 ± 0.37 | ND | 6.19 ± 0.44 | | |

TOFA stimulated expression mediated by GR/NUC, GR/PPAR and GR/NER hybrid receptors in a dose-dependent manner. In contrast to TOFA, the ligands Wy14643 and oleic acid maintained their expected receptor specificity and activated expression mediated by GR/PPAR and GR/NUC, but not by the GR/NER chimera. However, TOFA did not act as general stimulator of transcription since it did not stimulate expression of the MMTV-luciferase reporter gene after co-transfection of the native NUCI that does not interact with the MMTV-Luciferase reporter gene, and glucocorticoid receptors. The specific action of TOFA was further demonstrated by the fact that TOFA did not stimulate the expression of luciferase in cells transfected only with the MMTV-luciferase reporter gene, or with a reporter gene in which the expression was under the control of the promoter of SV40.

EXAMPLE 5

Activation of GR/PPAR by Fatty Acid Inhibitors

The ligand transcription assay mediated by GR/PPAR in COS cells was performed as described in Example 4. The cells were treated with TOFA and Cerulenin at 0.1, 1, 10 and 100 µM. Concentrations of cerulenin above 10 µM were toxic to the cells.

TOFA was originally developed as an inhibitor of fatty acid synthesis (Parker et al., 1977). We therefore tested whether cerulenin, an inhibitor of fatty acid synthesis which is structurally unrelated to TOFA, can mimic the transcriptional activation profile which was induced by TOFA. At concentrations that inhibit fatty acid synthesis, cerulenin did not stimulate transcription mediated by GR/PAR. These results suggest that the inhibition of fatty acid synthesis per se is unlikely to be responsible for the action of TOFA on this receptor family.

The results are depicted in Table 2, below.

TABLE 2

Activation of GR/PPAR Chimeric Receptor by Fatty Acid Inhibitors

| Treatment (μM) | Fold of Stimulation | |
|---|---|---|
| | TOFA | Cerulenin |
| 0 | 1.0 ± 0.14 | 1.0 ± 0.14 |
| 0.1 | 1.04 ± 0.14 | 1.03 ± 0.12 |
| 1.0 | 2.38 ± 0.16 | 1.13 ± 0.05 |
| 10.0 | 4.43 ± 0.23 | 0.58 ± 0.11 |
| 100 | 4.10 ± 0.52 | — |

EXAMPLE 6

Activation of GR/NER by Dopamine and TOFA in CV1 Cells

TOFA was found to activate transcription mediated by the ligand binding domain of the members of the PPAR family (NUC-I and PPAR) and the unrelated NER receptor. It is thus possible that TOFA may be interacting indirectly with these receptors in a ligand independent fashion akin to the interaction of dopamine with the COUP-TF and progesterone receptors (Power et al., 1991, 1991, 1992) that results with stimulation of transcription mediated by these receptors in CV1 cells. We therefore tested the activation of GR/NER by TOFA and dopamine in CV1 cells that express functional dopamine D1 receptors as measured by the elevation of cAMP levels win response to treatment with dopamine. TOFA stimulated the expression of luciferase mediated by the GR/NER chimera in CV1 cells.

The ligand dependent transcription assays were performed as described in Example 4, using CV1 cells in place of COS cells. The transfected CV1 cells were treated with dopamine, TOFA, or with a combination of TOFA and dopamine at the indicated concentrations and tested for luciferase activity.

The results are depicted in Table 3 below. The results indicate that dopamine did not stimulate transcription mediated by GR/NER as expected from its effects on COUP-TF and progesterone receptors. In contrast, we find that dopamine suppressed the transcription mediated by the GR/NER chimeric receptor. Furthermore, it partially inhibited the stimulation of transcription by TOFA. This suppression was not seen when GR/NER was transfected into COS-7 cells that do not express significant levels of the dopamine D1 receptors. These results indicate that there is cross talk between the dopamine receptor signally pathway and the NER receptor pathway.

TABLE 3

Activation of GR/NER in CV1 Cells

| Treatment (μM) | | |
|---|---|---|
| Dopamine | TOFA | Fold of Stimulation |
| 0 | 0 | 1.00 ± 0.08 |
| 0.1 | 0 | 1.28 ± 0.05 |
| 1.0 | 0 | 0.88 ± 0.11 |
| 10 | 0 | 0.55 ± 0.06 |
| 100 | 0 | 0.44 ± 0.14 |
| 100 | 10 | 1.40 ± 0.05 |
| 100 | 100 | 1.60 ± 0.07 |
| 0 | 100 | 3.70 ± 0.06 |

EXAMPLE 7

Activation of GR/NER by Dopamine and TOFA in COS-7 Cells

The ligand dependent transcription assays were performed as described in Example 4. The transfected COS cells were treated with dopamine, TOFA, or with the combination of TOFA and dopamine at the indicated concentrations and tested for luciferase activity.

The results are depicted in Table 4 below.

TABLE 4

Activation of GR/NER in COS-7 Cells

| Treatment (μM) | | |
|---|---|---|
| Dopamine | TOFA | Fold of Stimulation |
| 0 | 0 | 1.00 ± 0.07 |
| 0.1 | 0 | 1.10 ± 0.07 |
| 1.0 | 0 | 0.87 ± 0.06 |
| 10 | 0 | 0.84 ± 0.08 |
| 100 | 0 | 0.87 ± 0.11 |
| 100 | 10 | 3.24 ± 0.06 |
| 100 | 100 | 2.85 ± 0.07 |
| 0 | 100 | 3.36 ± 0.04 |

EXAMPLE 8

Effect of SCH 23390, a Dopamine D1 Receptor Antagonist, on the Activation of Luciferase Expression in GR/NER To further characterize the suppression of luciferase expression by dopamine, we tested whether a D1 dopamine receptor antagonist, SCH-23390, can prevent the suppression induced by dopamine. CV1 cells were co-transfected with the MMTV-Luciferase reporter gene (pJA358) and the GR/NER chimeric receptor as described in Example 4. The cells were treated with increasing amount of the dopamine D1 receptor antagonist SCH 23390 with or without 50 μM dopamine D1 receptor antagonist SCH 23390 with or without 50 μM dopamine.

The results depicted in Table 5 below indicate that treatment with SCH-23390 can reverse the inhibition of luciferase expression caused by dopamine. Moreover, the D1 dopamine antagonist SCH-23390 stimulated the transcription mediated by GR/NER. This further confirms the potential interaction between the NER receptor and dopamine receptor signaling pathways.

TABLE 5

Effect of SCH-23390 on the transcription mediated by the chimeric GR/NER receptor

| Treatment (μM) | Fold of Stimulation | |
|---|---|---|
| SCH-23390 | Control | Dopamine (50 μM) |
| 0.1 | 1.32 ± 0.15 | 0.59 ± 0.06 |
| 1.0 | 1.22 ± 0.11 | 0.55 ± 0.09 |
| 10.0 | 1.64 ± 0.38 | 0.83 ± 0.12 |
| 100 | 2.38 ± 0.19 | 2.61 ± 0.86 |

EXAMPLE 9

Stimulation of Neurite Differentiation of PC12 Cells by TOFA

To further study the influence of TOFA on the nervous system, we tested the effect of TOFA on the differentiation of PC12 cells. PC12 cells were plated at a density of approximately 100–200/mm$^2$ on collagen coated plates or dishes in RPMI medium supplemented with 10% horse serum, 5% fetal calf serum, 50 g/mL streptomycin, 50 U/mL penicillin in a water saturated atmosphere of 95% air and 5% $CO_2$, at 37° C. overnight. Medium was replaced with fresh RPMI containing 1.5% serum, 100 ng/mL NGF and the indicated concentration of TOFA or an equivalent volume of vehicle (DMSO) giving a final concentration of 0.1% DMSO.

At different time points during the treatment, cells were photographed or fixed with 10% formalin. Morphology was examined after four days of treatment with TOFA or vehicle (DMSO). The number of cells beating neurites and average length of neurites were determined with the aid of the Bioquant imaging system. Treatment with TOFA alone did not induce neurite outgrowth in PC12 cells (data not shown). However, as depicted in Table 6 below, NGF alone induced a 15% increase in the number of cells bearing neurites and these outgrowths reached a mean length of 20 μm. Treatment with NGF and TOFA increased the percentage of cells beating neurites to 78%. Maximal neurite generation is observed at a concentration of 10 μM TOFA. The addition of TOFA also increased the length of the developed neurites in a dose related fashion.

TABLE 6

Effects of TOFA on the Differentiation of PC-12 Cells

| | % Cells Bearing Neurites | Average length of neurites (μm) |
|---|---|---|
| Vehicle | 14.98 ± 1.68 | 19.78 ± 2.01 |
| 0.1 μM TOFA | 14.27 ± 3.51 | 23.67 ± 2.86 |
| 1.0 μM TOFA | 24.07 ± 3.06 | 28.63 ± 3.92 |
| 10 μM TOFA | 78.39 ± 4.89[a] | 32.43 ± 2.38[a] |

Cells were treated with vehicle (0.1% DMSO) or various concentrations of TOFA in the presence of 100 ng/mL NGF for 4 days, and then fixed with 10% formalin. At least eighty cells from eight wells were analyzed in each group. The results are shown as the mean ±SEM. [a]$p<0.01$, versus vehicle by Dunnetts test.

EXAMPLE 10

Effect of TOFA on a Dopamine D1 Receptor Antagonist (SCH 23390) Induced Catalepsy Rats were pretreated with 0.4 mg/kg TOFA or with carrier (S.C.). Twenty-four hours later, the rats were challenged with 0.5 mg/kg SCH23390, a Dopamine D1 antagonist, and the duration of catalepsy was monitored.

Catalepsy was determined by a modification of the Bar method (Undie and Friedman, 1988). A steel bar, 1.1 cm in diameter and 50 cm long, was suspended at a height of 10 cm above the working surface. Three sides of the bench around the bar were walled off with brown cardboard, and the linings on the bench surface were selected to be of the same color with the cardboard walls. The animal's hind limbs were freely placed on the bench, the fail laid out to the back, and the forelimbs placed over the bar. The length of time a rat stayed up on the bar was noted up to a preset cut-off point of 120 s. The time was counted off upon observing any of the following actions: (1) the animal came off, placing its two forepaws on the bench, (2) the animal climbed onto or over the bar with both hind limbs, (3) the animal initiated locomotion along or around the bar. Subsequently, time readings were translated into scores by awarding a score of 1 for each successfully completed 5 s on the bar. For each observation time, catalepsy scores were averaged for all the animals in a group to give the Mean Score of the group at that observation time. Further, the scores for each animal at all the observation times were added to give the total score for that animal. The mean of this last group of numbers was called the Mean Total Score of the group.

Catalepsy scores were analyzed by computer in accordance with the statistical procedures outlined by Winer, B. J.: Statistical principles in experimental design. McGraw-Hill, New York, pp. 10–428, 1971. Generally, for a given set of comparisons, observations were subjected to an appropriate analysis of variance followed by two-tailed Dunnett or Student's t-tests to detect differences between treatment groups.

The data are shown in Table 7 below:

TABLE 7

Effect of TOFA on SCH 23390 Induced Catalepsy

| Pretreatment (Time = 0) | Treatment | Catalepsy Duration (seconds) |
|---|---|---|
| TOFA | none | 0 |
| control | SCH 23390 | 3.1 ± 1.3 |
| TOFA | SCH 23390 | 75 ± 17.8 |

The data shown above indicate that TOFA pretreatment markedly increased the duration of the SCH 23390-induced catalepsy by at least 25 fold.

EXAMPLE 11

Effect of TOFA on a Muscarinic Receptor Agonist (Pilocarpine) Induced Catalepsy

Rats were pretreated with 0.4 mg/kg TOFA or with carrier (S.C.). Twenty-four hours later, the rats were challenged with 16 mg/kg Pilocarpine, an agonist of the muscarinic cholinergic receptor, and the duration of catalepsy was monitored as described in Example 10.

The data are shown in Table 8 below:

TABLE 8

Effect of TOFA on Pilocarpine Induced Catalepsy

| Pretreatment | Treatment | Catalepsy Duration (seconds) |
|---|---|---|
| TOFA control | none | 0 |
|  | Pilocarpine | 27.3 ± 3.6 |
| TOFA | Pilocarpine | 84.1 ± 9.6 |

The data shown above indicate that TOFA pretreatment increased the duration of the Pilocarpine-induced catalepsy by 3 fold.

EXAMPLE 12

Effect of TOFA on a Dopamine D2 Receptor Antagonist (Haloperidol) Drug Induced Catalepsy

Rats were pretreated with 0.4 mg/kg TOFA or with carrier (S.C.). Twenty-four hours later, the rats were challenged with 0.1 mg/kg Haloperidol, an antagonist of the Dopamine D2 Receptor, and the duration of catalepsy was monitored as described in Example 10.

The data are shown in Table 9 below:

TABLE 9

Effect of TOFA on Haloperidol Induced Catalepsy

| Pretreatment | Treatment | Catalepsy Duration (seconds) |
|---|---|---|
| TOFA control | none | 0 |
|  | Haloperidol | 20.3 ± 6.7 |
| TOFA | Haloperidol | 28.9 ± 4.5 |

The data shown above indicate that TOFA pretreatment did not significantly affect Haloperidol-induced catalepsy.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

---

What is claimed is:

1. A method for the treatment of Alzheimer's disease comprising the administration of a pharmacologically effective amount of 5-(tetradecyloxy)-2-furan carboxylic acid or a pharmaceutically acceptable salt or ester thereof to a patient in need of such treatment.

2. The method of claim 1 wherein an NGF-potentiating amount of 5-(tetradecyloxy)-2-furan carboxylic acid or a pharmaceutically acceptable salt or ester thereof is administered.

3. The method of claim 2 further comprising the administration of a pharmacologically effective amount of NGF.

4. A method for the treatment of Alzheimer's disease by potentiating the activity of a dopamine D1 receptor antagonist which comprises administering a potentiating amount of 5-(tetradecyloxy)-2-furan carboxylic acid or a pharmaceutically acceptable salt or ester thereof and a pharmacologically effective amount of a dopamine D1 receptor antagonist to a patient in need of such treatment.

5. The method according to claim 4 wherein the dopamine D1 receptor antagonist is SCH23390:

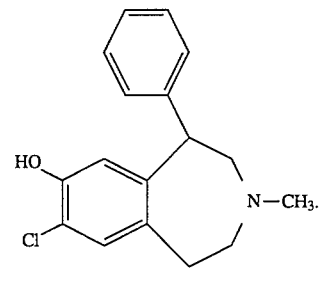

SCH23390

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2030 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
CAAGAAGTGG CGAAGTTACC TTTGAGGGTA TTTGAGTAGC GGCGGTGTGT CAGGGGCTAA      60
AGAGGAGGAC GAAGAAAAGC AGAGCAAGGG AACCCAGGGC AACAGGAGTA GTTCACTCCG     120
CGAGAGGCCG TCCACGAGAC CCCCGCGCGC AGGCATGAGC CCCGCCCCCC ACGCATGAGC     180
CCCGCCCCCC GCTGTTGCTT GGAGAGGGGC GGGACCTGGA GAGAGGCTGC TCCGTGACCC     240
CACCATGTCC TCTCCTACCA CGAGTTCCCT GGATACCCCC CTGCCTGGAA ATGGCCCCCC     300
TCAGCCTGGC GCCCCTTCTT CTTCACCCAC TGTAAAGGAG GAGGGTCCGG AGCCGTGGCC     360
CGGGGGTCCG GACCCTGATG TCCCAGGCAC TGATGAGGCC AGCTCAGCCT GCAGCACAGA     420
CTGGGTCATC CCAGATCCCG AAGAGGAACC AGAGCGCAAG CGAAAGAAGG GCCCAGCCCC     480
GAAGATGCTG GGCCACGAGC TTTGCCGTGT CTGTGGGGAC AAGGCCTCCG GCTTCCACTA     540
CAACGTGCTC AGCTGCGAAG GCTGCAAGGG CTTCTTCCGG CGCAGTGTGG TCCGTGGTGG     600
GGCCAGGCGC TATGCCTGCC GGGGTGGCGG AACCTGCCAG ATGGACGCTT TCATGCGGCG     660
CAAGTGCCAG CAGTGCCGGC TGCGCAAGTG CAAGGAGGCA GGGATGAGGG AGCAGTGCGT     720
CCTTTCTGAA GAACAGATCC GGAAGAAGAA GATTCGGAAA CAGCAGCAGC AGGAGTCACA     780
GTCACAGTCG CAGTCACCTG TGGGGCCGCA GGGCAGCAGC AGCTCAGCCT CTGGGCCTGG     840
```

```
GGCTTCCCCT GGTGGATCTG AGGCAGGCAG CCAGGGCTCC GGGGAAGGCG AGGGTGTCCA      900
GCTAACAGCG GCTCAAGAAC TAATGATCCA GCAGTTGGTG GCGGCCCAAC TGCAGTGCAA      960
CAAACGCTCC TTCTCCGACC AGCCCAAAGT CACGCCCTGG CCCCTGGGCG CAGACCCCA      1020
GTCCCGAGAT GCCCGCCAGC AACGCTTTGC CCACTTCACG GAGCTGGCCA TCATCTCAGT     1080
CCAGGAGATC GTGGACTTCG CTAAGCAAGT GCCTGGTTTC CTGCAGCTGG GCCGGGAGGA     1140
CCAGATCGCC CTCCTGAAGG CATCCACTAT CGAGATCATG CTGCTAGAGA CAGCCAGGCG     1200
CTACAACCAC GAGACAGAGT GTATCACCTT CTTGAAGGAC TTCACCTACA GCAAGGACGA     1260
CTTCCACCGT GCAGGCCTGC AGGTGGAGTT CATCAACCCC ATCTTCGAGT TCTCGCGGGC     1320
CATGCGGCGG CTGGGCCTGG ACGACGCTGA GTACGCCCTG CTCATCGCCA TCAACATCTT     1380
CTCGGCCGAC CGGCCCAACG TGCAGGAGCC GGGCCGCGTG GAGGCGTTGC AGCAGCCCTA     1440
CGTGGAGGCG CTGCTGTCCT ACACGCGCAT CAAGAGGCCG CAGGACCAGC TGCGCTTCCC     1500
GCGCATGCTC ATGAAGCTGG TGAGCCTGCG CACGCTGAGC TCTGTGCACT CGGAGCAGGT     1560
CTTCGCCTTG CGGCTCCAGG ACAAGAAGCT GCCGCCTCTG CTGTCGGAGA TCTGGGACGT     1620
CCACGAGTGA GGGGCTGGCC ACCCAGCCCC ACAGCCTTGC CTGACCACCC TCCAGCAGAT     1680
AGACGCCGGC ACCCCTTCCT CTTCCTAGGG TGGAAGGGGC CCTGGGCGAG CCTGTAGACC     1740
TATCGGCTCT CATCCCTTGG GATAAGCCCC AGTCCAGGTC CAGGAGGCTC CCTCCCTGCC     1800
CAGCGAGTCT TCCAGAAGGG GTGAAAGGGT TGCAGGTCCC GACCACTGAC CCTTCCCGGC     1860
TGCCCTCCCT CCCCAGCTTA CACCTCAAGC CCAGCACGCA GCGTACCTTG AACAGAGGGA     1920
GGGGAGGACC CATGGCTCTC CCCCCCTAGC CCGGGAGACC AGGGGCCTTC CTCTTCCTCT     1980
GCTTTTATTT AATAAAAATA AAACAGAAA  AAAAAAAAA  AAAAAAAAA                2030
```

(2) INFORMATION FOR SEQ ID NO:2:

(i) SEQUENCE CHARACTERISTICS:
        (A) LENGTH: 461 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

```
Met Ser Ser Pro Thr Thr Ser Ser Leu Asp Thr Pro Leu Pro Gly Asn
 1               5                  10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
                    100                 105                 110

Arg Ser Val Val Arg Gly Gly Ala Arg Arg Tyr Ala Cys Arg Gly Gly
```

|     |     |     | 115 |     |     |     |     | 120 |     |     |     |     | 125 |     |     |
| --- | --- | --- | --- | --- | --- | --- | --- | --- | --- | --- | --- | --- | --- | --- | --- |
| Gly | Thr<br>130 | Cys | Gln | Met | Asp | Ala<br>135 | Phe | Met | Arg | Arg | Lys<br>140 | Cys | Gln | Gln | Cys |
| Arg<br>145 | Leu | Arg | Lys | Cys | Lys<br>150 | Glu | Ala | Gly | Met | Arg<br>155 | Glu | Gln | Cys | Val | Leu<br>160 |
| Ser | Glu | Glu | Gln | Ile<br>165 | Arg | Lys | Lys | Lys | Ile<br>170 | Arg | Lys | Gln | Gln | Gln<br>175 | Gln |
| Glu | Ser | Gln | Ser<br>180 | Gln | Ser | Gln | Ser | Pro<br>185 | Val | Gly | Pro | Gln | Gly<br>190 | Ser | Ser |
| Ser | Ser | Ala<br>195 | Ser | Gly | Pro | Gly | Ala<br>200 | Ser | Pro | Gly | Gly | Ser<br>205 | Glu | Ala | Gly |
| Ser | Gln<br>210 | Gly | Ser | Gly | Glu<br>215 | Gly | Glu | Gly | Val | Gln<br>220 | Leu | Thr | Ala | Ala | Gln |
| Glu<br>225 | Leu | Met | Ile | Gln | Gln<br>230 | Leu | Val | Ala | Ala | Gln<br>235 | Leu | Gln | Cys | Asn | Lys<br>240 |
| Arg | Ser | Phe | Ser | Asp<br>245 | Gln | Pro | Lys | Val | Thr<br>250 | Pro | Trp | Pro | Leu | Gly<br>255 | Ala |
| Asp | Pro | Gln | Ser<br>260 | Arg | Asp | Ala | Arg | Gln<br>265 | Gln | Arg | Phe | Ala | His<br>270 | Phe | Thr |
| Glu | Leu | Ala<br>275 | Ile | Ile | Ser | Val | Gln<br>280 | Glu | Ile | Val | Asp | Phe<br>285 | Ala | Lys | Gln |
| Val | Pro<br>290 | Gly | Phe | Leu | Gln | Leu<br>295 | Gly | Arg | Glu | Asp | Gln<br>300 | Ile | Ala | Leu | Leu |
| Lys<br>305 | Ala | Ser | Thr | Ile | Glu<br>310 | Ile | Met | Leu | Leu | Glu<br>315 | Thr | Ala | Arg | Arg | Tyr<br>320 |
| Asn | His | Glu | Thr | Glu<br>325 | Cys | Ile | Thr | Phe | Leu<br>330 | Lys | Asp | Phe | Thr | Tyr<br>335 | Ser |
| Lys | Asp | Asp | Phe<br>340 | His | Arg | Ala | Gly | Leu<br>345 | Gln | Val | Glu | Phe | Ile<br>350 | Asn | Pro |
| Ile | Phe | Glu<br>355 | Phe | Ser | Arg | Ala | Met<br>360 | Arg | Arg | Leu | Gly | Leu<br>365 | Asp | Asp | Ala |
| Glu | Tyr<br>370 | Ala | Leu | Leu | Ile | Ala<br>375 | Ile | Asn | Ile | Phe | Ser<br>380 | Ala | Asp | Arg | Pro |
| Asn<br>385 | Val | Gln | Glu | Pro | Gly<br>390 | Arg | Val | Glu | Ala | Leu<br>395 | Gln | Gln | Pro | Tyr | Val<br>400 |
| Glu | Ala | Leu | Leu | Ser<br>405 | Tyr | Thr | Arg | Ile | Lys<br>410 | Arg | Pro | Gln | Asp | Gln<br>415 | Leu |
| Arg | Phe | Pro | Arg<br>420 | Met | Leu | Met | Lys | Leu<br>425 | Val | Ser | Leu | Arg | Thr<br>430 | Leu | Ser |
| Ser | Val | His<br>435 | Ser | Glu | Gln | Val | Phe<br>440 | Ala | Leu | Arg | Leu | Gln<br>445 | Asp | Lys | Lys |
| Leu | Pro<br>450 | Pro | Leu | Leu | Ser | Glu<br>455 | Ile | Trp | Asp | Val | His<br>460 | Glu |     |     |     |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CGAATTCTGT GAGGGCTGCA ARGSC    25

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
CGAATTCTGT GAGGGCTGCA ARGSCTTCTT C                                31
```

( 2 ) INFORMATION FOR SEQ ID NO:5:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
Gly Gly Ala Ala Thr Thr Cys Arg Ala Ala Asn Cys Cys Asn Gly Gly
 1           5                      10                     15

Asn Ala Asn Asn Asn Asn Tyr Thr Thr Asn Gly Cys Arg Ala Ala
            20                  25                  30
```